United States Patent [19]
Launay et al.

[11] Patent Number: 6,004,994
[45] Date of Patent: Dec. 21, 1999

[54] HETEROCYCLIC DIARYLMETHYLENE DERIVATIVES, METHODS OF PREPARING THEM AND THEIR USES IN THERAPEUTICS

[75] Inventors: Michele Launay, Rueil-Malmaison; Eric Nicolai, Rueil Malmaison; Jean-Marie Teulon, La Celle Saint Cloud, all of France

[73] Assignee: Laboratoires UPSA, Agen, France

[21] Appl. No.: 09/248,379

[22] Filed: Feb. 11, 1999

[30] Foreign Application Priority Data

Feb. 27, 1998 [FR] France ................................. 98 02384
Feb. 27, 1998 [FR] France ................................. 98/02384

[51] Int. Cl.[6] ........................ C01D 207/26; A61K 31/40
[52] U.S. Cl. .................... 514/424; 514/445; 548/551; 549/66
[58] Field of Search ............... 548/551; 549/66; 514/424, 445

[56] References Cited

U.S. PATENT DOCUMENTS 5,461,158 10/1995 Mita .......................................... 548/551

*Primary Examiner*—Robert Gerstl
*Attorney, Agent, or Firm*—Barry J. Marenberg

[57] ABSTRACT

The present invention relates to compounds of the formula:

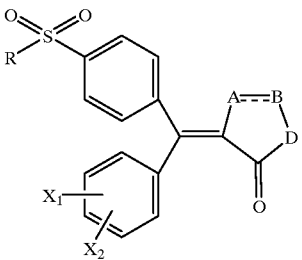

and their use in therapeutics, especially as medicaments with anti-inflammatory and analgesic properties.

12 Claims, No Drawings

HETEROCYCLIC DIARYLMETHYLENE DERIVATIVES, METHODS OF PREPARING THEM AND THEIR USES IN THERAPEUTICS

The present invention relates to the heterocyclic diarylmethylene derivatives of general formula (I) below and to their addition salts, particularly pharmaceutically acceptable addition salts, as novel products.

One of the arachidonic acid biotransformation pathways is the cyclooxygenase pathway, which makes it possible to transform arachidonic acid into PGG2 and then PGH2. Recent work on the cloning and sequencing of cyclooxygenase has revealed the presence of two isoenzymes, namely cyclooxygenase-1 (COX-1) and cyclooxygenase-2 (COX-2), in several species and particularly in man. The first is a constitutive enzyme which is expressed in the majority of tissues, while the second, which is expressed in a few tissues such as the brain, is inducible in the majority of tissues by numerous products, in particular by the cytokines and the mediators produced during the inflammatory reaction. Each enzyme has a different role and the inhibition of COX-1 or COX-2 will not have identical consequences. The inhibition of COX-1 will cause a decrease in the prostaglandins participating in homeostasis which can give rise to side effects. The inhibition of COX-2 will cause a decrease in the prostaglandins produced in an inflammatory situation. Thus the selective inhibition of COX-2 makes it possible to obtain a well-tolerated anti-inflammatory.

The compounds of the invention make it possible to achieve this selective inhibition. The compounds in question consequently have a very valuable pharmacological profile insofar as they possess anti-inflammatory and analgesic properties while being remarkably well tolerated, especially in gastric terms. They will be particularly indicated in the treatment of inflammatory phenomena and in the treatment of pain.

An example of their use which may be mentioned is the treatment of arthritis, especially rheumatoid arthritis, spondylitis, gouty arthritis, osteoarthritis, juvenile arthritis, autoimmune diseases and lupus erythematosus. They will also be indicated in the treatment of bronchial asthma, dysmenorrhea, tendinitis, bursitis, dermatological inflammations such as psoriasis, eczema, burns and dermatitis. They can also be used in the treatment of gastrointestinal inflammations, Crohn's disease, gastritis and ulcerative colitis, in the prevention of cancer, especially adenocarcinoma of the colon, in the prevention of neurodegenerative diseases, particularly Alzheimer's disease, in the prevention of cerebral ischaemia and epilepsy, and in the prevention of premature labour.

Their analgesic properties also enable them to be used for any pain symptoms, especially in the treatment of myalgia, articular pain or neuralgia, dental pain, herpes zoster and migraine, in the treatment of rheumatic complaints and pain of cancerous origin, and also as complementary treatments for infectious and febrile states.

The present invention further relates to the method for the preparation of said products and to their application in therapeutics.

These heterocyclic diarylmethylene derivatives are characterised in that they are of general formula (I):

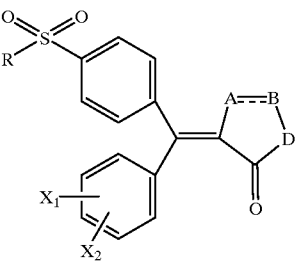

Formula (I)

in which:
R represents:
  a lower alkyl radical having 1 to 6 carbon atoms,
  a lower haloalkyl radical having 1 to 6 carbon atoms,
  an $NH_2$ group,
$X_1$ and $X_2$ independently represent:
  a hydrogen atom,
  a halogen atom,
  a lower alkyl radical having 1 to 6 carbon atoms,
  a lower O-alkyl radical having 1 to 6 carbon atoms,
  a trifluoromethyl radical, or together may even form a methylenedioxy group,
A represents:
  $CH_2$ group,
  a nitrogen atom,
  a sulphur atom,
B represents:
  a $CH_2$ group,
  a CH—R' group, R' representing a lower alkyl radical having 1 to 6 carbon atoms,
  a C=S group,
  a C-Φ group, Φ being an aromatic ring, in the case in which A represents a nitrogen atom and in the case in which the bond between A and B is a double bond,
D represents:
  an oxygen atom when A represents a heteroatom,
  a sulphur atom,
  an N—R" group, in which R" represents:
    a hydrogen atom,
    a lower alkyl radical having 1 to 6 carbon atoms,
    an allyl radical,
    $C_3$–$C_7$ cycloalkyl radical,
    a $(CH_2)n$-Y radical, n being an integer from 1 to 4 and Y representing an OH or COOR''' group, R''' representing a hydrogen atom or a lower alkyl radical having 1 to 6 carbon atoms,
    a $(CH_2)m$-Ar group, m being an integer from 0 to 4 and Ar representing a phenyl ring non-substituted or substituted with 1 to 3 halogen atoms or 1 to 3 lower alkyl radicals having 1 to 6 carbon atoms.

The above-mentioned derivatives of formula (I) can be in the form of addition salts, particularly pharmaceutically acceptable addition salts.

In the description and claims, lower alkyl radical is understood as meaning a linear or branched hydrocarbon chain having 1 to 6 carbon atoms. A lower alkyl radical is for example a methyl, ethyl, propyl, isopropyl, butyl, isobutyl, tert-butyl, pentyl, isopentyl, hexyl, or isohexyl radical.

$C_3$–$C_7$ cycloalkyl radical is understood as meaning a saturated cyclic hydrocarbon radical, preferably a cyclopropyl, cyclobutyl, cyclopentyl, cyclohexyl or cycloheptyl radical.

Halogen is understood as meaning a chlorine, bromine, iodine or fluorine atom.

Lower haloalkyl radical is understood as meaning an alkyl radical having 1 to 6 carbon atoms of which 1 to 7 hydrogen atoms have been substituted with 1 to 7 halogen atoms. A lower haloalkyl radical is for example a trifluoromethyl radical, a 2,2,2-trifluoroethyl radical, a pentafluoroethyl radical, a 2,2-difluoro 3,3,3-trifluoropropyl radical, a heptafluoropropyl radical, or a chloromethyl or bromomethyl radical.

Aromatic ring is understood as meaning any aromatic ring having 5 to 6 carbon atoms or heteroatoms. An aromatic ring is for example a phenyl, pyridyl, thienyl, furanyl, or pyrimidyl ring.

Advantageously, the derivatives in accordance with the invention are derivatives of the above-mentioned formula (I) in which:

R represents:
  a methyl radical,
  an $NH_2$ group, $X_1$ and $X_2$ independently represent:
  a hydrogen atom,
  a halogen atom,
  a lower alkyl radical having 1 to 6 carbon atoms,
  a lower O-alkyl radical having 1 to 6 carbon atoms, A represents:
  $CH_2$ group,
  a nitrogen atom,
  a sulphur atom, B represents:
  a $CH_2$ group,
  a CH—R' group, R' representing a lower alkyl radical having 1 to 6 carbon atoms,
  a C=S group,
  a C-Φ group, Φ being a phenyl radical in the case in which A represents a nitrogen atom and in the case in which the bond between A and B is a double bond.

D represents:
  an oxygen atom when A represents a nitrogen atom,
  a sulphur atom,
  an N—R" group, in which R" represents:
    a hydrogen atom,
    a lower alkyl radical having 1 to 6 carbon atoms,
    an allyl radical,
    a $C_3$–$C_7$ cycloalkyl radical,
    a $(CH_2)n$-Y radical, n being an integer from 1 to 4 and Y representing an OH or COOR''' group, R''' representing a hydrogen atom or a lower alkyl radical having 1 to 6 carbon atoms,
    a $(CH_2)m$-Ar group, m being an integer from 0 to 4 and Ar representing a phenyl ring non-substituted or substituted with a halogen atom or a lower alkyl radical having 1 to 6 carbon atoms.

Advantageously, within the context of the present invention, a compound of formula (I) will be used in which at least one of the following conditions is met:

R represents a methyl radical or an —$NH_2$ group, $X_1$ represents a chlorine atom and $X_2$ represents a hydrogen atom or a chlorine atom.

A and B each represent a $CH_2$ group,

D represents a sulphur atom or an N—$CH_3$, N—$C_2H_5$, N-(3-Cl benzyl) group.

The particularly preferred compounds of the invention are those which are selected from the following compounds:

(Z)-3-[1-(4-chlorophenyl)-1-[4-(methylsulphonyl)phenyl]methylene]dihydro-2(3H)-thiophenone

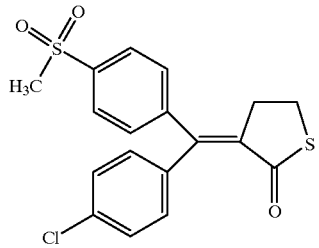

(Z)-3-[1-(4-chlorophenyl)-1-[4-(methylsulphonyl)phenyl]methylene]-1-ethyl-pyrrolidin-2-one

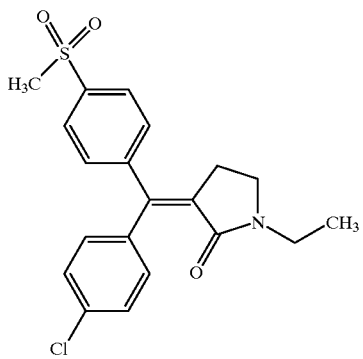

(Z)-3-[1-(3,4-dichlorophenyl)-1-[4-(methylsulphonyl)phenyl]methylene]-1-methyl-pyrrolidin-2-one

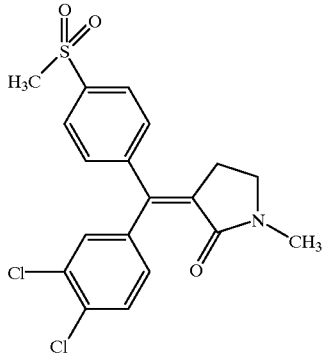

(Z)-4-[(3,4-dichlorophenyl)-(1-methyl-2-oxo-pyrrolidin-3-ylidene)methyl]-benzenesulphonamide

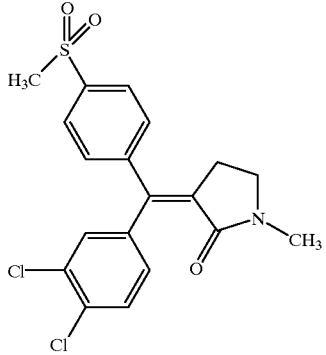

-continued (Z)-3-[1-(4-chlorophenyl)-1-[4-(methylsulphonyl)phenyl]
methylene]-1-(3-chlorophenylmethyl)-pyrrolidin-2-one

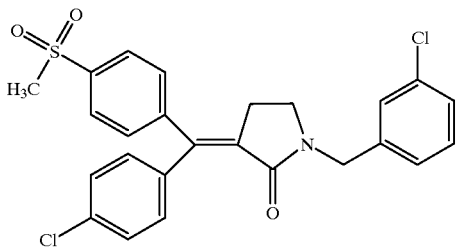

According to the invention, the compounds of formula (I) can be synthesised in the following manner:

A reaction of condensation of a benzophenone of formula (II) (which is known or the preparation of which can be found in the patent application WO 97/37984), Formula (II)

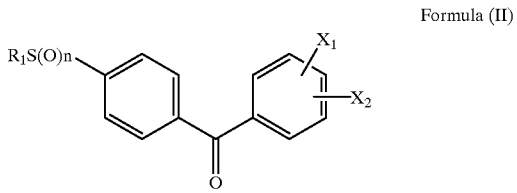

in which $X_1$ and $X_2$ are as defined above, n equals 0 or 2, $R_1$ is a lower alkyl radical having 1 to 6 carbon atoms, a lower haloalkyl radical having 1 to 6 carbon atoms and can be an NH-tert-butyl radical when n=2, onto a compound of formula (III)

Formula (III)

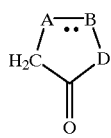

in which A, B, D are as defined above, in the presence of a base such as potassium tert-butoxide or sodium hydride, or in the presence of titanium tetrachloride and pyridine, in a solvent such as dimethylformamide, tetrahydrofuran or dichloromethane, which leads directly to the derivatives of formula (IV)

Formula (IV)

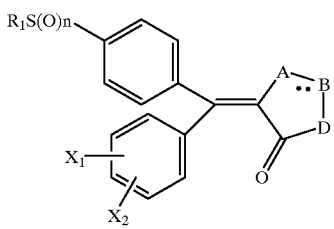

in which A, B, D, $X_1$, $X_2$, $R_1$ and n are as defined above, or to the derivatives of formula (V)

Formula (V)

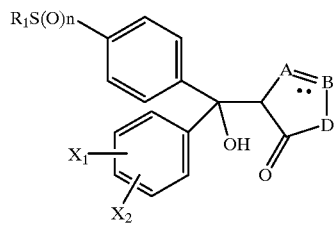

in which A, B, D, $X_1$, $X_2$ and $R_1$ and n are as defined above, which, in this case, are treated with a dehydrating agent such as sulphuric acid in acetic acid or even trifluoroacetic acid in dichloromethane in order to lead to the derivatives of formula (IV).

The derivatives of formula (IV) or of formula (V), in which n equals zero and $R_1$ is a lower alkyl radical or a lower haloalkyl radical, can be transformed into derivatives of corresponding formulae in which n=2 by means of an oxidising agent such as a peracid, for example meta-chloroperbenzoic acid, it being possible for this oxidation in the case of derivatives of formula (V) to be carried out either before or after the dehydration. The derivatives of formula (IV) in which n=2 and $R_1$ represents an NH-tert-butyl group can be transformed into corresponding derivatives of formula (I), in which $R_1$ represents an $NH_2$ group, by heating under the reflux, in the presence of p-toluenesulphonic acid, of a solvent such as toluene for example.

The derivatives of formula (I) in which A and B represent a $CH_2$ group and D represents a sulphur atom can be prepared from an alkyl 3,3-diaryl-2-(2-hydroxyethyl)-2-propionate derivative of formula (VI), Formula (VI)

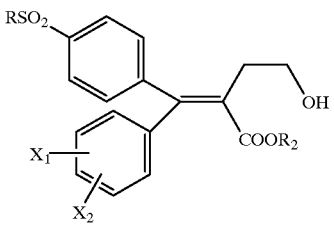

in which R, $X_1$ and $X_2$ are as defined above and $R_2$ represents a lower alkyl group having 1 to 6 carbon atoms, the preparation of which is described in the patent applications WO 97/37984 and FR 96.12234, by a Mitsunobu reaction by treating the alcohol ester with diisopropyl azodicarboxylate, triphenylphosphine and thiolacetic acid, followed by a cyclisation in acidic medium.

In the case in which the heterocycle of formula (III) represents a pyrrolidinone ring, the preferred method for obtaining the derivative of formula (I) in which D represents an NH group, consists in using N-triphenylmethyl-pyrrolidin-2-one as derivative of formula (III) and in dehydrating the derivative of formula (V) formed, with trifluoroacetic acid in dichloromethane, enabling obtaining the derivative of formula (I) or of formula (IV) directly in which D represents an NH group, the triphenylmethane or trityl protecting group being removed under the action of the acid.

This derivative of formula (I) or of formula (IV) in which A, B and D represent $CH_2$, $CH_2$ and NH respectively:

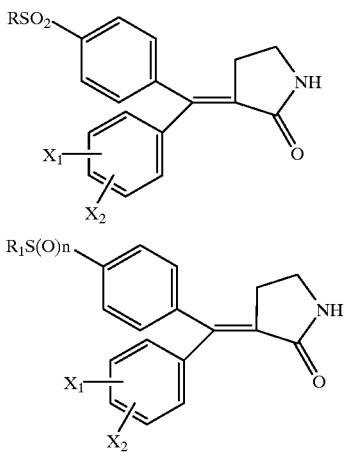

can be used for preparing derivatives of corresponding formulae in which D represents an N—R" group, R" being defined as above, the substitution of the NH group being then carried out by a phase transfer reaction, in the presence of tetrabutylammonium bromide and finely ground potassium hydroxide, by the action of a halo-R" or even an acrylic derivative.

A mixture of Z and E isomers is generally obtained from the condensation reactions of compounds of formula (II) and of formula (III).

These two isomers can be separated by fractional recrystallisation of the mixture or of a mixture of salts, or by other methods of separation known to the person skilled in the art, such as chromatography.

The addition salts of the compounds of formula (I), in particular those which have an acid function, can be obtained by the reaction of these compounds with a base or with an amino acid according to a method known per se. Amongst the bases which can be used, sodium hydroxide, potassium hydroxide, potassium or sodium carbonate and sodium or potassium bicarbonate can be mentioned, and amongst the amino acids, lysine for example.

The compounds of formula (I) as defined above as well as their addition salts, in particular their pharmaceutically acceptable addition salts, are cyclooxygenase-2 inhibitors and possess a very good anti-inflammatory and analgesic activity coupled with an excellent tolerance, particularly gastric tolerance.

The compounds which possess the highest activity are in general those in the formula of which the C=0 group is found in the trans- position with respect to the phenyl bearing the $SO_2R$ group.

These properties justify their application in therapeutics and the invention further relates, by way of drugs, to the products as defined by formula (I) above, as well as to their addition salts, in particular their pharmaceutically acceptable addition salts.

Thus, the invention also covers a pharmaceutical composition characterised in that it comprises a pharmaceutically effective amount of at least one compound of formula (I) such as defined above or one of its pharmaceutically acceptable addition salts incorporated in a pharmaceutically acceptable excipient, vehicle or carrier.

These compositions can be administered via the buccal, rectal, parenteral, transdermal, ocular, nasal or auricular route.

These compositions can be solid or liquid and can be presented in the pharmaceutical forms commonly used in human medicine, such as, for example, simple or coated tablets, gelatine capsules, granules, suppositories, injectable preparations, transdermal systems, eye drops, aerosols and sprays, and ear drops. They are prepared by the customary methods. The active principle, which consists of a pharmaceutically effective amount of at least one compound of formula (I) as defined above or one of its pharmaceutically acceptable addition salts can be incorporated therein together with excipients normally employed in pharmaceutical compositions, such as talc, gum arabic, lactose, starch, magnesium stearate, polyvidone, cellulose derivatives, cocoa butter, semi-synthetic glycerides, aqueous or non-aqueous vehicles, fats of animal or vegetable origin, glycols, various wetting agents, dispersants or emulsifiers, silicone gels, certain polymers or copolymers, preservatives, flavourings and colours.

The invention also covers a pharmaceutical composition with anti-inflammatory and analgesic activity which can be used especially as a favourable treatment for inflammatory phenomena and pain, said composition being characterised in that it comprises a pharmaceutically effective amount of at least one compound of formula (I) above or one of its pharmaceutically acceptable addition salts incorporated in a pharmaceutically acceptable excipient, vehicle or carrier.

In one embodiment, a pharmaceutical composition with anti-inflammatory and analgesic activity is prepared which may be used especially as a favourable treatment for various inflammations and pain.

The invention also covers a pharmaceutical composition useful in the prevention of cancer, in particular adenocarcinoma of the colon, in the prevention of neurodegenerative diseases, particularly Alzheimer's disease, in the prevention of cerebral ischaemia and epilepsy, and in the prevention of premature labour.

In one implementation variant, a composition is formulated as gelatine capsules or tablets containing a dose of 1 mg to 1000 mg, or as injectable preparations containing a dose of 0.1 mg to 500 mg. It is also possible to use compositions formulated as suppositories, ointments, creams, gels, aerosol preparations, transdermal preparations or plasters.

The invention also covers a method of therapeutic treatment for mammals. characterised in that a therapeutically effective amount of at least one compound of formula (I) as defined above or one of its pharmaceutically acceptable addition salts is administered to the said mammal. In one variant of this method of treatment, the compound of formula (I) either by itself or in association with a pharmaceutically acceptable excipient, is formulated as gelatine capsules or tablets containing a dose of 1 mg to 1000 mg for oral administration, as injectable preparations containing a dose of 0.1 mg to 500 mg or as suppositories, ointments, creams, gels or aerosol preparations.

This method affords especially a favourable treatment for inflammatory phenomena and pain.

In human and animal therapeutics, the compounds of formula (I) and their salts can be administered by themselves or in association with a physiologically acceptable excipient, in any form, in particular orally in the form of gelatine capsules or tablets, or parenterally in the form of injectable solutions. It is possible to envisage other forms of administration such as suppositories, ointments, creams, gels or aerosol preparations.

As will be clearly apparent from the pharmacological experiments given at the end of the description, the compounds according to the invention can be administered in human therapeutics, in the above-mentioned indications, orally in the form of tablets or gelatine capsules containing a dose of 1 mg to 1000 mg, or parenterally in the form of injectable preparations containing a dose of 0.1 mg to 500 mg, in one or more daily dosage units, for an adult with an average weight of 60 to 70 kg.

In animal therapeutics, the daily dose which can be used is between 0.1 mg and 100 mg per kg.

Further characteristics and advantages of the invention will be understood more clearly by reading the following Examples, which in no way imply a limitation but are given by way of illustration.

EXAMPLE 1

3-[(4-chlorophenyl)-hydroxy-[4-(methylthio)phenyl] methyl]-1-methyl-pyrrolidin-2-one Formula (V): $X_1$=4-Cl, $R_1$=$CH_3$, n=0, A-B=—$CH_2$—$CH_2$—, D=N—$CH_3$ 26.9 g (0.228 mole, 3 eq.) of potassium tert-butoxide are added portionwise to 36.6 ml (0.38 mole, 5 eq.) of N-methyl pyrrolidin-2-one under mechanical stirring. An exothermic effect develops upon each addition with the appearance of a red-pink colour. Once the addition is complete, stirring is kept up for 20 minutes, the reaction medium is then cooled to 0° C. 20 g (0.076 mole) of 4-chloro-4'-methylthiobenzophenone are then added portionwise. The reaction medium is stirred 2 h at ambient temperature and then hydrolysed on ice. After extraction with t-butyl methyl ether, the organic phase is washed with water, dried over magnesium sulphate and concentrated. The residue is taken up into isopropyl ether to give 24.7 g of 3-[(4-chlorophenyl)-hydroxy-[4-(methylthio)phenyl]methyl]-1-methyl-pyrrolidin-2-one as white crystals of melting point MPt= 120° C.

According to the same method, the following compounds are obtained of formula (V) in which: A-B represents $CH_2$—$CH_2$

| Example | $X_1$ | $X_2$ | $R_1$ | n | D | MPt (° C.) |
|---|---|---|---|---|---|---|
| 2 | 4-F | H | $CH_3$ | 0 | N—$CH_3$ | brown oil |
| 3 | 3-Cl | 4-Cl |  | 2 | N—$CH_3$ | 96–100 (off-white) |
| 4 | 4-Cl | H |  | 2 | N—$CH_3$ | brown oil |
| 5 | 4-Cl | H | $CH_3$ | 0 | N—$CH_2CH_3$ | brown oil |
| 6 | H | H | $CH_3$ | 0 | N—$CH_3$ | 131 (off-white) |
| 7 | 3-Cl | 4-Cl | $CH_3$ | 0 | N—$CH_3$ | 141 (off-white) |
| 8 | 4-O$CH_3$ | H | $CH_3$ | 0 | N—$CH_3$ | >130 (off-white) |
| 9 | 3-$CH_3$ | 4-F | $CH_3$ | 0 | N—$CH_3$ | brown oil |
| 10 | 4-Cl | H | $CH_3$ | 0 | N-benzyl | 98 |
| 11 | 4-Cl | H | $CH_3$ | 0 | N—$CH(CH_3)_2$ | oil |

EXAMPLE 12

3-[(4-chlorophenyl)-hydroxy-[4-(methylthio)phenyl] methyl]-1-cyclohexyl-pyrrolidin-2-one Formula (V): $X_1$=4-Cl, $R_1$=$CH_3$, n=0, A-B=—$CH_2$—$CH_2$—, D=N-cyclohexyl 31.6 ml (0.19 mole) of N-cyclohexyl-pyrrolidin-2-one and 20 ml of anhydrous dimethylformamide are placed in a four-necked flask with mechanical stirring. 11.2 g (0.095 mole, 2.5 eq.) of potassium tert-butoxide are added portionwise at ambient temperature. Upon each addition, an exothermic effect develops as well as a purple coloration.

Stirring is continued for 30 minutes and the reaction medium is then cooled to 10° C. and treated portionwise with 10 g (0.038 mole) of 4-chloro-4'-methylthiobenzophenone.

Once the addition is complete, the temperature rises to ambient temperature and stirring is continued for 2 h. The reaction medium is hydrolysed on ice and extracted with t-butyl methyl ether. The organic phase is washed with water, dried over magnesium sulphate and then concentrated to give an oily residue which is purified on a silica column (eluent ethyl acetate/cyclohexane 2/8). 15.5 g of 3-[(4-chlorophenyl)-hydroxy-[4-(methylthio)phenyl]methyl]-1-cyclohexyl-pyrrolidin-2-one are thereby obtained as an orange oil.

EXAMPLE 13

3-[(4-chlorophenyl)-hydroxy-[4-(methylthio)phenyl]-methyl]-1-triphenylmethyl-pyrrolidin-2-one Formula (V): $X_1$=4-Cl, $R_1$=$CH_3$, n=0, A-B=—$CH_2$—$CH_2$—, D=N-trityl or N-triphenylmethyl According to the method of Example 12 but by replacing the dimethylformamide with tetrahydrofuran, 2.8 g of 3-[(4-chlorophenyl)-hydroxy-[4-(methylthio)phenyl]-methyl]-1-triphenylmethyl-pyrrolidin-2-one are obtained as a yellow orange oil after purification on a silica column (eluent $CH_2Cl_2$), and used as such in what follows, from 10.3 g (0.0314 mole) of N-triphenylmethylpyrrolidin-2-one and 2.06 g (0.00785 mole) of 4-chloro-4'-methylthiobenzophenone.

According to the same method, the following compounds are obtained of formula (V) in which: A-B represents $CH_2$—$CH_2$

| Example | $X_1$ | $X_2$ | $R_1$ | n | D | MPt (° C.) |
|---|---|---|---|---|---|---|
| 14 | 4-Cl | H | $CH_3$ | 0 | N-(3-$CH_3$ benzyl) | orange oil |
| 15 | 4-Cl | H | $CH_3$ | 0 | N-(2-Cl benzyl) | brown oil |
| 16 | 4-Cl | H | $CH_3$ | 0 | N-(3-Cl benzyl) | brown oil |
| 17 | 4-Cl | 3-Cl | $CH_3$ | 0 | N-benzyl | brown oil |
| 18 | 4-Cl | H | $CH_3$ | 0 | N-(4-Br benzyl) | brown oil |
| 19 | 4-Cl | 3-Cl | N-tBu | 2 | N-phenethyl | brown oil |
| 20 | 4-Cl | 3-Cl | N-tBu | 2 | N-benzyl | brown oil |
| 21 | 4-Cl | H | $CH_3$ | 0 | N-phenethyl | brown oil |

EXAMPLE 22

3-[(4-chlorophenyl)-hydroxy-[4-(methylthio)phenyl] methyl]-1-(2-hydroxyethyl)-pyrrolidin-2-one Formula (V): $X_1$=4-Cl, $R_1$=$CH_3$, n=0, A-B=—$CH_2$—$CH_2$—, D=N—$CH_2CH_2OH$ 6.5 g (0.05 mole) of N-(2-hydroxyethyl)pyrrolidin-2-one are dissolved in 100 ml of tetrahydrofuran and placed in a three-necked flask with mechanical stirring, and then treated with 2.0 g (0.05 mole) of NaH (60 %). The very thick reaction medium obtained is stirred 30 minutes and then 3.6 g (0.03 mole) of potassium tert-butoxide are added. Gradual dissolution is observed. After having warmed the solution 15 minutes at 50° C., it is cooled to 15° C. 2.6 g of 4-chloro-4'-methylthiobenzophenone are added portionwise. After one night at ambient temperature, the reaction medium is hydrolysed on ice, acidified with 10 ml of concentrated hydrochloric acid, and decanted. The aqueous phase is extracted with t-butyl methyl ether. The organic phases are combined, washed with water, dried over magnesium sulphate and concentrated. The residue obtained is taken up into pentane and then washed with ether. 1.28 g of 3-[(4-chlorophenyl)-hydroxy-[4-(methylthio)phenyl]methyl]-1-(2-hydroxyethyl)-pyrrolidin-2-one are obtained as a beige solid of melting point 141° C.

EXAMPLE 23
3-[(4-chlorophenyl)-hydroxy-[4-(methylsulphonyl)phenyl]methyl]-1-methyl-pyrrolidin-2-one Formula (V): $X_1$=4-Cl, $R_1$=$CH_3$, n=2, A-B=—$CH_2$—$CH_2$—, D=N—$CH_3$ 5.5 g (0.015 mole) of 3[(4-chlorophenyl-hydroxy-[4-(methylthio)phenyl]methyl]-1-methyl-pyrrolidin-2-one are placed in solution in 60 ml of dichloromethane, cooled to 0–5° C. and treated dropwise with a solution of 7.5 g (0.03 mole, 2 eq) of 70% m-chloroperbenzoic acid in 40 ml of dichloromethane.

After 2 h, the solution is washed with a 10% sodium bicarbonate solution, then with water, and dried over magnesium sulphate. 6.1 g of 3-[(4-chlorophenyl)-hydroxy-[4-(methylsulphonyl)phenyl]methyl]-1-methyl-pyrrolidin-2-one are obtained as a white foam after concentration.

According to the same method, the following compounds are obtained of formula (V) in which: A-B represents $CH_2$—$CH_2$

| Example | $X_1$ | $X_2$ | $R_1$ | n | D | MPt (° C.) |
|---|---|---|---|---|---|---|
| 24 | 4-Cl | H | $CH_3$ | 2 | N-cyclohexyl | white solid |
| 25 | 4-Cl | H | $CH_3$ | 2 | N-$CH_2CH_2OH$ | 154 (white) |
| 26 | 4-Cl | H | $CH_3$ | 2 | N-benzyl | (off-white) |
| 27 | 4-Cl | H | $CH_3$ | 2 | N-$CH_2CH_3$ | pale yellow oil |

EXAMPLE 28
3-[1-(4-chlorophenyl)-1-[4-(methylsulphonyl)phenyl]methylene]-1-methyl-pyrrolidin-2-one Formula (I): $X_1$=4-Cl, R=$CH_3$, A-B=—$CH_2$—$CH_2$—, D=N—$CH_3$ 6.7 g (0.017 mole) of 3-[(4-chlorophenyl)-hydroxy-[4-(methylsulphonyl) phenyl]methyl]-1-methyl-pyrrolidin-2-one are dissolved in 15 ml of acetic acid. 0.25 ml of sulphuric acid are added and the solution heated 2 h 30 at 80° C. After cooling, the medium is poured onto ice and extracted with dichloromethane. The organic phase is washed with a 10% sodium bicarbonate solution, then with water, and dried over magnesium sulphate. After concentration, 6 g of the mixture of isomers are obtained which are separated by chromatography on an $SiO_2$ column (eluent $CH_2Cl_2$/Acetone—9/1).

2.7 g of (Z)-3-[1-(4-chlorophenyl)-1-[4-(methylsulphonyl)phenyl]-methylene]-1-methyl-pyrrolidin-2-one as a white solid of melting point 194–195° C. and 1.7 g of (E)-3-[1-(4-chlorophenyl)-1-[4-(methylsulphonyl)phenyl]methylene]-1-methyl-pyrrolidin-2-one as a white solid of melting point 192–193° C. are thus obtained after recrystallisation from isopropanol.

According to the same method, the following compounds are obtained of formula (I) in which: A-B represents $CH_2$—$CH_2$

| Example | $X_1$ | $X_2$ | R | D | Z Isomer (MPt ° C.) | E Isomer (MPt ° C.) |
|---|---|---|---|---|---|---|
| 29 | 4-Cl | H | $CH_3$ | N-cyclohexyl | 209–210 | 213.5–215 |
| 30 | 4-Cl | H | $CH_3$ | N-$CH_2CH_2OAc$ | Pale yellow foam | Pale yellow foam |
| 31 | 4-Cl | H | $CH_3$ | N-benzyl | foam | 152.5–153 |
| 32 | 4-Cl | H | $CH_3$ | N-$CH_2CH_3$ | 172–173 | 155–156 |
| 33 | 4-Cl | 3-Cl | $NH_2$ | N-$CH_3$ | 209 | |

EXAMPLE 34
3-[1-(4-fluorophenyl)-1-[4-(methylthio)phenyl]methylene]-1-methyl-pyrrolidin-2-one Formula (IV): $X_1$=4-F, $R_1$=$CH_3$, n=0, A-B=—$CH_2$—$CH_2$—, D=N—$CH_3$ 11.8 g of 3-[(4-fluorophenyl)-hydroxy-[4-(methylthio)phenyl]methyl]-1-methyl-pyrrolidin-2-one are dissolved in 150 ml of dichloromethane and treated dropwise with 6.2 ml (2.5 eq.) of trifluoroacetic acid. The reaction is exothermic. After 1 h at ambient temperature, the solution is washed with a 10% sodium bicarbonate solution, then with water, dried and concentrated. The residue is purified by chromatography on $SiO_2$ (eluent $CH_2Cl_2$/acetone 9/1). 4.86 g of the mixture of isomers of 3-[1-(4-fluorophenyl)-1-[4-(methylthio)phenyl]methylene]-1-methyl-pyrrolidin-2-one are thus obtained as a brown oil.

According to the same method. The following compounds are obtained of (IV) in which: A-B represents $CH_2$—$CH_2$

| Example | $X_1$ | $X_2$ | $R_1$ | n | D | MPt (° C.) |
|---|---|---|---|---|---|---|
| 35 | 4-Cl | H | $CH_3$ | 0 | H (the deprotection of the N-trityl is simultaneous) | white solid |
| 36 | 4-Cl | 3-Cl | $CH_3$ | 0 | N-$CH_3$ | 130 |
| 37 | H | H | $CH_3$ | 0 | N-$CH_3$ | (brown oil) |
| 38 | 4-$OCH_3$ | H | $CH_3$ | 0 | N-$CH_3$ | (brown oil) |
| 39 | 4-F | 3-$CH_3$ | $CH_3$ | 0 | N-$CH_3$ | 105-110 (beige) |
| 40 | 4-Cl | H | $CH_3$ | 0 | N-isopropyl | (clear brown oil) |
| 41 | 4-Cl | H | $CH_3$ | 0 | N-phenethyl | (brown oil) |
| 42 | 4-Cl | 3-Cl | $CH_3$ | 0 | N-benzyl | (brown oil) |
| 43 | 4-Cl | H | $CH_3$ | 0 | N-(3-Cl-benzyl) | (brown oil) |
| 44 | 4-Cl | H | $CH_3$ | 0 | N-(2-Cl-benzyl) | (red oil) |
| 45 | 4-Cl | H | $CH_3$ | 0 | N-(3-$CH_3$-benzyl) | (orange oil) |
| 46 | 4-Cl | H | $CH_3$ | 0 | N-(4-Br-benzyl) | (brown oil) |
| 47 | 4-Cl | H | $CH_3$ | 0 | N-benzyl | (brown oil) |
| 48 | 4-Cl | H | $CH_3$ | 0 | N-$CH_3$ | (brown oil) |

EXAMPLE 49
Ethyl [3-[1-(4-chlorophenyl)-1-[4-(methylthio)phenyl]methylene]-2-oxo-pyrrolidin-1-yl]acetate Formula (IV): $X_1$=4-Cl, $R_1$=$CH_3$, n=0, A-B=—$CH_2$—$CH_2$—, D=N—$CH_2$COOEt 3.5 g (0.0106 mole) of 3-[1-(4-chlorophenyl)-1-[4-(methylthio)phenyl]methylene]-pyrrolidin-2-one are placed in suspension in 150 ml of toluene. 0.7 g of tetrabutylammonium bromide (0.2 eq.), 0.6 g (1 eq) of finely ground potassium hydroxide and 1.2 ml (1 eq.) of ethyl bromoacetate are added at ambient temperature and the medium stirred for 15 h.

After washing with water, the toluene is concentrated and the residue purified on silica (eluent ethyl acetate/cyclohexane 5/5) to give 3.5 g of ethyl [3-[1-(4-chlorophenyl)-1-[4-(methylthio)phenyl]methylene]-2-oxo-pyrrolidin-1-yl] acetate as a yellow oil used as such in what follows.

EXAMPLE 50
Ethyl 3-[3-[1-(4-chlorophenyl)-1-[4-(methylthio)phenyl]methylene]-2-oxo-pyrrolidin-1-yl]propanoate Formula (IV): $X_1$=4-Cl, $R_1$=$CH_3$, n=0, A-B=—$CH_2$—$CH_2$—, D=N—$CH_2CH_2$COOEt 4.0 g (0.012 mole) of ) 3-[1-(4-chlorophenyl)-1-[4-(methylthio)phenyl]methylene]-pyrrolidin-2-one are placed in suspension in 160 ml of toluene. 0.8 g of tetrabutylammonium bromide (0.2 eq.), 0.67 g (1 eq) of finely ground potassium hydroxide and 1.3 ml (1 eq.) of ethyl acrylate are added at ambient temperature and the medium stirred for 4 h.

After washing with water, the toluene is concentrated and the residue purified on silica (eluent ethyl acetate/cyclohexane 5/5) to give 3.8 g of ethyl 3-[3-[1-(4-chlorophenyl)-1-[4-(methylthio)phenyl]methylene]-2-oxo-pyrrolidin-1-yl]propanoate as a yellow oil used as such in what follows.

EXAMPLE 51
3-[1-(4-fluorophenyl)-1-[4-(methylsulphonyl)phenyl]methylene]-1-methyl-pyrrolidin-2-one Formula (I): $X_1$=4-F, R=$CH_3$, A-B=—$CH_2$—$CH_2$—, D=N—$CH_3$ 4.86 g (0.0148 mole) of 3-[1-(4-fluorophenyl)-1-[4-(methylthio)phenyl]methylene]-1-methyl-pyrrolidin-2-one are dissolved in 60 ml of dichloromethane at 0–5° C. and treated dropwise with a solution of 6.8 g (2 eq.) of 70% m-chloroperbenzoic acid in 60 ml of dichloromethane. After 2 h, the reaction is stopped and the solution obtained is washed with a 10% sodium bicarbonate solution, then with water, dried and concentrated. 5.5 g of the mixture of isomers are obtained which are separated by chromatography on $SiO_2$ (eluent $CH_2Cl_2$/Acetone 9/1). 1.2 g of (E)-3-[1-(4-fluorophenyl)-1-[4-(methylsulphonyl)phenyl]methylene]-1-methyl-pyrrolidin-2-one as white crystals of melting point 199–200° C. and 1.3 g of (Z)-3-[1-(4-fluorophenyl)-1-[4-(methylsulphonyl)phenyl]methylene]-1-methyl-pyrrolidin-2-one as white crystals of melting point 181–182° C. are thus obtained after recrystallisation from isopropanol.

According to the same method. The following compounds are obtained of formula (I) in which: A-B represents $CH_2$—$CH_2$

| Example | $X_1$ | $X_2$ | R | D | Z isomer (MPt ° C.) | E isomer (MPt ° C.) |
|---|---|---|---|---|---|---|
| 52 | 4-Cl | H | $CH_3$ | NH | 241–242 | 265–266 |
| 53 | 4-Cl | 3-Cl | $CH_3$ | N-$CH_3$ | 191–192 | 205–206 |
| 54 | H | H | $CH_3$ | N-$CH_3$ | 220–222 | 223 |
| 55 | 4-O$CH_3$ | H | $CH_3$ | N-$CH_3$ | 176–177 | 175–176 |
| 56 | 4-F | 3-$CH_3$ | $CH_3$ | N-$CH_3$ | 149 | 188 |
| 57 | 4-Cl | H | $CH_3$ | N-$CH_2$COOEt | 140–141 | |
| 58 | 4-Cl | H | $CH_3$ | N-$(CH_2)_2$—$CO_2$Et | foam | yellow oil |
| 59 | 4-Cl | H | $CH_3$ | N-CH$(CH_3)_2$ | 191–193 | 195–197 |
| 60 | 4-Cl | H | $CH_3$ | N-phenethyl | 205–206 | 91–96 |
| 61 | 4-Cl | 3-Cl | $CH_3$ | N-benzyl | 208 | foam |
| 62 | 4-Cl | H | $CH_3$ | N-3-Cl benzyl | foam | foam |
| 63 | 4-Cl | H | $CH_3$ | N-2-Cl benzyl | 180 | 184 |
| 64 | 4-Cl | H | $CH_3$ | N-3-$CH_3$ benzyl | 174 | |
| 65 | 4-Cl | H | $CH_3$ | N-4-Br benzyl | 182 | |
| 66 | 4-Cl | H | $CH_3$ | N-benzyl | foam | |

EXAMPLE 67
(Z)-3-[3-[1-(4-chlorophenyl)1-[4-(methylsulphonyl)phenyl]methylene]-2-oxo-pyrrolidin-1-yl]propanoic acid Formula (I): $X_1$=4-Cl, R=$CH_3$, A-B=—$CH_2$—$CH_2$—, D=N—$CH_2CH_2$COOH 1 g (0.0045 mole) of ethyl (Z)-3-[3-[1-(4-chlorophenyl)-1-[4-(methylsulphonyl)phenyl]methylene]-2-oxo-pyrrolidin-1-yl]propanoate are placed in a solution in a mixture of 15 ml of ethanol and 20 ml of water and treated with 0.28 g (1.5 eq.) of sodium hydroxide. The medium is heated at 50° C. for 4 h. The ethanol was evaporated off and the aqueous phase is then extracted with ethyl acetate, acidified with a dilute hydrochloric acid solution, and extracted with dichloromethane. The organic phase is washed with water dried and concentrated. The residue is taken up into t-butyl methyl ether. 1.6 g of (Z)-3-[3-[1-(4-chlorophenyl)-1-[4-(methylsulphonyl)phenyl]methylene]-2-oxo-pyrrolidin-1-yl]propanoic acid are thus obtained as a beige solid of melting point 178–179° C.

EXAMPLE 68
(Z)-3-[1-(4-chlorophenyl)-1-[4-(methylsulphonyl)phenyl]methylene]-1-(2-hydroxyethyl)-pyrrolidin-2-one Formula (I): $X_1$=4-Cl, R=CH$_3$, A-B=—CH$_2$—CH$_2$—, D=N—CH$_2$CH$_2$OH 1 g (0.0022 mole) of (Z)-2-[3-[1-(4-chlorophenyl)-1-[4-(methylsulphonyl)phenyl]methylene]-2-oxo-pyrrolidin-1-yl]ethyl acetate are placed in solution in a mixture of 13 ml of ethanol and 11 ml of water and treated with 0.1 g (1.1 eq.) of sodium hydroxide. The medium is stirred at ambient temperature for 4 h, then the ethanol is evaporated off. The aqueous phase is extracted with dichloromethane. The organic phase is washed with water, dried and concentrated. The residue is taken up into t-butyl methyl ether. 0.7 g of (Z)-3-[1-(4-chlorophenyl)-1-[4-(methylsulphonyl)phenyl]methylene]-1-(2-hydroxyethyl)-pyrrolidin-2-one are thus obtained as a yellow solid of melting point 187–188° C.

EXAMPLE 69
4-[(4-chlorophenyl)-(1-methyl-2-oxo-pyrrolidin-3-ylidene)methyl]benzenesulphonamide Formula (I): $X_1$=4-Cl, $R_1$=NH$_2$, A-B=—CH$_2$—CH$_2$—, D=N—CH$_3$ 6 g (0.013 mole) of N-t-butyl-4-[(4-chlorophenyl)-hydroxy-(1-methyl-2-oxo-pyrrolidin-3-yl)-methyl]-benzenesulphonamide are refluxed for 5 h in 60 ml of toluene in the presence of 100 mg of p-toluenesulphonic acid. After cooling, the toluene phase is washed with a 10% sodium bicarbonate solution, then with water, dried over magnesium sulphate and concentrated.

The residue is chromatographed on a Silica column (eluent ethyl acetate/cyclohexane—8/2) to give 1.58 g of (Z)-4-[(4-chlorophenyl)-(1-methyl-2-oxopyrrolidin-3-ylidene) methyl]-benzenesulphonamide as an off-white solid of melting point 205–206° C. and 1.0 g of (E)-4-[(4-chlorophenyl)-(1-methyl-2-oxo -pyrrolidin-3-ylidene)methyl]benzenesulphonamide as an off-white solid of melting point 209–211° C.

According to the same method, the following compounds are obtained of formula (I) in which: A-B represents CH$_2$—CH$_2$

| Example | $X_1$ | $X_2$ | R | D | Z isomer (MPt ° C.) | E Isomer (MPt ° C.) |
|---|---|---|---|---|---|---|
| 70 | 4-Cl | 3-Cl | NH$_2$ | N-phenethyl | 212 | 219 |
| 71 | 4-Cl | 3-Cl | NH$_2$ | N-benzyl | 175–176 | 180–181 |

EXAMPLE 72
(Z)-3-[1-(4-chlorophenyl)-1-[4-(methylsulphonyl)phenyl]methylene]-1-(propen-3-yl)-pyrrolidin-2-one Formula (I): $X_1$4-Cl, $R_1$=CH$_3$, A-B=—CH$_2$—CH$_2$—, D=N—CH$_2$CH=CH$_2$ 1.6 g (0.0044 mole) of (Z)-3-[1-(4-chlorophenyl)-1-[4-(methylsulphonyl)phenyl]methylene]-pyrrolidin-2-one are placed in suspension in a mixture of 150 ml of toluene and 100 ml of tetrahydrofuran. 0.3 g of tetrabutylammonium bromide (0.2 eq.), 0.25 g (1 eq) of finely ground potassium hydroxide and 0.4 ml (1 eq.) of allyl bromide are added at ambient temperature and the medium stirred for 3 days.

After washing with water, the toluene is concentrated and the residue purified on a silica column (eluent CH$_2$Cl$_2$/acetone 95/5) and crystallised in isopropyl ether to give 0.2 g of (Z)-3-[1-(4-chlorophenyl)-1-[4-(methylsulphonyl)phenyl]methylene]-1-(propen-3-yl)-pyrrolidin-2-one as a white solid of melting point MPt=116° C.

EXAMPLE 73
3-[(4-chlorophenyl)-hydroxy-[4-(methylthio)phenyl]methyl]-1,5-dimethyl-pyrrolidin-2-one Formula (V): $X_1$=4-Cl, $R_1$=CH$_3$, n=0, A-B=—CH$_2$—CH(CH$_3$)—, D=N—CH$_3$ 22.6g (0.19 mole) of 1,5-dimethyl pyrrolidin-2-one and 10 ml of anhydrous tetrahydrofuran are placed in a four-necked flask with mechanical stirring. 18 g (4 eq.) of potassium tert-butoxide are added portionwise at ambient temperature. Upon each addition, an exothermic effect develops as well as an orange coloration.

Stirring is continued for 30 minutes and the reaction medium is then cooled to 0° C. and treated portionwise with 10 g (0.038 mole) of 4-chloro-4'-thiomethylbenzophenone. The suspension thickens and becomes yellow.

Once the addition is complete, 10 ml of tetrahydrofuran are added and the temperature is allowed to rise to ambient temperature. Stirring is continued for 3 h. The reaction medium is hydrolysed on ice and extracted with t-butyl methyl ether. The organic phase is washed with a dilute hydrochloric acid solution, then with water, dried over magnesium sulphate and concentrated. 12 g of 3-[(4-chlorophenyl)-hydroxy-[4-(methylthio)phenyl]methyl]-1,5-dimethyl-pyrrolidin-2-one are thus obtained as a brown oil used as such in what follows.

EXAMPLE 74
3-[1-(4-chlorophenyl)-1-[4-(methylthio)phenyl]methylene]-1,5-dimethyl-pyrrolidin-2-one Formula (IV): $X_1$=4-Cl, $R_1$=CH$_3$, n=0, A-B=—CH$_2$—CH(CH$_3$)—, D=N—CH$_3$ 12 g of 3-[(4-chlorophenyl)-hydroxy-[4-(methylthio)phenyl]methyl]-1,5-dimethyl-pyrrolidin-2-one are dissolved in 120 ml of dichloromethane and treated dropwise with 7.7 ml (2.5 eq.) of trifluoroacetic acid. The reaction is exothermic. After 6 h at ambient temperature, the solution is washed with a 10% sodium bicarbonate solution, then with water, dried and concentrated. 10.4 g of the mixture of isomers of 3-[1-(4-chlorophenyl)-1-[4-(methylthio)phenyl]methylene]-1,5-dimethyl-pyrrolidin-2-one are thus obtained as a brown oil used as such in what follows.

EXAMPLE 75
3-[1-(4-chlorophenyl)-1-[4-(methylsulphonyl)phenyl]methylene]-1,5-dimethyl-pyrrolidin-2-one Formula (I): $X_1$=4-Cl, R=CH$_3$, A-B=—CH$_2$—CH(CH$_3$)—, D=N—CH$_3$ 10.4 g (0.03 mole) of 3-[1-(4-chlorophenyl)-1-[4-(methylthio)phenyl]methylene]-1,5-dimethyl-pyrrolidin-2-one are dissolved in 100 ml of dichloromethane at 0–5° C. and treated dropwise with a solution of 13.3 g (2 eq.) of 70% m-chloroperbenzoic acid in 60 ml of dichloromethane. After one night, the reaction is stopped and the solution obtained is washed with a 10% sodium bicarbonate solution, then with water, dried and concentrated. 10.8 g of the mixture of isomers are obtained which are separated by chromatography on SiO$_2$ (eluent CH$_2$Cl$_2$/Acetone 95/5). 3.1 g of (E)-3-[1-(4-chlorophenyl)-1-[4-(methylsulphonyl)phenyl]

methylene]-1,5-dimethyl-pyrrolidin-2-one as an off-white solid of melting point 219–220° C. and 3.88 g of (Z)-3-[1-(4-chlorophenyl)-1-[4-(methylsulphonyl)phenyl] methylene]-1,5-dimethyl-pyrrolidin-2-one as a white solid of melting point 154–155° C. are thus obtained after having taken up the solid obtained into isopropyl ether.

EXAMPLE 76
2-phenyl-5-oxazolone

Formula (III): A=N, B=C-phenyl, D=O, A and B being linked by a double bond

A mixture of 80 g of hippuric acid and 400 ml of acetic anhydride is heated at 70° C. for two hours. The solution is then brought to ambient temperature and the acetic anhydride is evaporated off under vacuum. The residue is taken up into petroleum ether and crystallises. The crystals are filtered off with suction and washed with petroleum ether and with ethanol to give 25 g of 2-phenyl-5-oxazolone as crystals of melting point 90° C.

EXAMPLE 77
(E)-4-[1-(4-chlorophenyl)-1-[4-(methylsulphonyl)phenyl) methylene]-2-phenyl-5(4H)-oxazolone Formula (I): R=$CH_3$, $X_1$=4-Cl, $X_2$=H, A=N, B=C-phenyl D=O, A and B being linked by a double bond A solution of 11 ml of titanium tetrachloride in 27 ml of carbon tetrachloride is added dropwise at −10° C. to 110 ml of anhydrous tetrahydrofuran. Once the addition is complete, a solution of 14.7 g of 4-chloro-4'-(methylsulphonyl)benzophenone (the preparation of which is described in the document WO97/37984) in 50 ml of anhydrous tetrahydrofuran is added dropwise in keeping the temperature below 0° C. A mixture of 8.05 g of 2-phenyl-5(4H)-oxazolone, 16 ml of pyridine and 25 ml of anhydrous tetrahydrofuran is then added dropwise at 0° C. The mixture is stirred 2 hours at this temperature, then brought to ambient temperature and 50 ml of water are added. After decanting, the organic phase is washed with water then dried over magnesium sulphate and evaporated off under vacuum. The residue crystallises in an acetone/t-butyl methyl ether mixture and is chromatographed on silica in an acetone/dichloromethane mixture (0.3/10) to give 5 g of (E)-4-[1-(4-chlorophenyl)-1-[4 -(methylsulphonyl)phenyl] methylene]-2-phenyl-5-oxazolone as crystals of melting point 226° C.

EXAMPLE 78
(E)-5-[1-(4-chlorophenyl)-1-[4-(methylsulphonyl)phenyl] methylene]-2-thioxo-4(5H)-thiazolidinone Formula (I): R=$CH_3$, $X_1$=4-Cl, X=H, A=S, B=C=S, D=O, A and B being linked by a single bond A solution of 11 ml of titanium tetrachloride in 27 ml of dichloromethane is added dropwise at 0° C. onto 200 ml of anhydrous tetrahydrofuran. Once the addition is complete, a solution of 14.7 g of 4-chloro-4'-(methylsulphonyl) benzophenone in 150 ml of dichloromethane is added dropwise at 0° C. A mixture of 6.6 g of rhodanine, 16 ml of pyridine and 20 ml of anhydrous tetrahydrofuran is then added dropwise always at 0° C. The mixture is stirred 2 hours at this temperature, then brought to ambient temperature and 200 ml of water are added. After decanting, the organic phase is washed with a saturated sodium chloride solution, dried over magnesium sulphate and evaporated under vacuum. The residue is chromatographed on silica gel in an acetone/dichloromethane mixture (1/10) to give 1.2 g of (E)-5-[1-(4chlorophenyl)-1-[4-(methylsulphonyl)phenyl] methylene]-2-thioxo-4(5H)-thiazolidinone as crystals of melting point 252° C.

EXAMPLE 79
Ethyl (Z)-2-[1-(4-chlorophenyl)-1-[4-(methylsulphonyl) phenyl]methylene]-4-acetylthio-butanoate To a solution of 19.5 g of triphenylphosphine in 300 ml of tetrahydrofuran are added at 0° C., 14.8 g of diisopropyl azodicarboxylate. The mixture is stirred 30 minutes and a precipitate appears. A mixture of 5.3 ml of thiolacetic acid, 15 g of ethyl (Z)-2-[1-(4-chlorophenyl)-1-[4-(methylsulphonyl)phenyl]methylene]-4-hydroxy-butenoate, the preparation of which is described in the document WO97/37984, and 100 ml of tetrahydrofuran, is then added at 0° C. The reaction medium is stirred 1 hour at 0° C. and then 6 h at ambient temperature. After addition of ether and water, the organic phase is dried over magnesium sulphate and evaporated under vacuum. The residue is chromatographed on silica gel in dichloromethane. The oil obtained crystallises in isopropyl ether to give 14.4 g of ethyl (Z)-2-[1-(4-chlorophenyl)-1-[4-(methylsulphonyl)phenyl] methylene]-4-acetyl thiobutanoate as crystals of melting point 90° C.

EXAMPLE 80
(Z)-3-[1-(4-chlorophenyl)-1-[4-(methylsulphonyl)phenyl] methylene]-4,5-dihydro-2(3H)-thiophenone Formula (I): R=$CH_3$, $X_1$=4-Cl, $X_2$=H, A=B=$CH_2$, D=S, A and B being linked by a single bond A solution of 12 g of ethyl (Z)-2-[1-(4-chlorophenyl)-1-[4-(methylsulphonyl) phenyl]methylene]-4-acetylthiobutanoate, prepared in Example 79, in 120 ml of ethanol and 10 ml of concentrated hydrochloric acid is heated under reflux for 8 hours.

After addition of water, the crystals formed are filtered off with suction and taken up into 150 ml of toluene. After addition of 100 mg of 4-toluenesulphonic acid, the mixture is heated under reflux for 8 hours to give 8.5 g of (Z)-3-[1-(4-chlorophenyl)-1-[4-(methylsulphonyl)phenyl] methylene]-4,5-dihydro-2(3H)-thiophenone as crystals of melting point 183° C.

PHARMACOLOGY

The analgesic activity of the compounds of the Examples was evaluated according to the method of arthritis with kaolin.

Method

Analgesic Activity

The analgesic activity is evaluated in rats by the test of arthritis with kaolin. Thirty minutes after intra-articular administration of an aqueous 10% suspension of kaolin, the product is administered orally at a rate of 1 ml 100 g (n=10 animals per dose). The results are expressed in the form of $ED_{50}$, the dose in mg/kg which induces 50% decrease of the maximal quotations obtained in the control batch, calculated by linear regression.

| Example | Arthritis with kaolin $ED_{50}$ (mg/kg) |
| --- | --- |
| 31 Z isomer | 18.5 |
| 80 Z isomer | 13.7 |

Inhibition of the COX-1 and COX-2 Enzymatic Activities

The molecule studied is preincubated for 10 minutes at 25° C. with 2 U of COX-1 (purified enzyme from ram seminal vesicles) or 1 U of COX-2 (purified enzyme from ewe placenta). Arachidonic acid (6 $\mu$M for COX-1, 4 $\mu$M for COX-2) is added to the reaction medium and incubation is carried out for 5 minutes at 25° C. When incubation has ended, the enzymatic reaction is stopped by the addition of 1 N HCl and the PGE2 produced is deter mined by EIA.

For certain examples, the results are expressed as percentage inhibition of the COX-1 and COX-2 enzymatic activities, and correspond to mean±standard deviation on the average of 4 determinations. For other examples, the results are expressed in the form of $IC_{50}$, the concentration in $\mu$M corresponding to 50% inhibition of the maximal enzymatic activity upon COX-1 and COX-2 (n=1 to 4 determinations).

| Example | Inhibition of COX-1 % inhibition $10^{-4}$M | Inhibition of COX-2 | |
| --- | --- | --- | --- |
| | | % inhibition $10^{-5}$M | IC50 ($\mu$M) |
| 28 Z isomer | 6 | 77 | 2.945 |
| 29 Z isomer | 72 | 86 | — |
| 30 Z isomer | — | 56 | — |
| 31 Z isomer | 88 | 88 | — |
| 32 Z isomer | 13 | 84 | 2.530 |
| 33 Z isomer | — | 70 at $10^{-6}$M | 0.393 |
| 53 Z isomer | 36 | 92 | — |
| 55 E isomer | — | 44 | — |
| 56 Z isomer | — | 53 | — |
| 60 Z isomer | 32 | 52 at $10^{-6}$M | — |
| 61 Z isomer | — | 80 at $10^{-6}$M | 0.229 |
| 62 Z isomer | 79 | 91 | — |
| 63 Z isomer | 83 | 88 | — |
| 64 Z isomer | — | 59 | — |
| 65 Z isomer | — | 83 | — |
| 77 E isomer | 90 | 77 | 2.83 |
| 78 E isomer | 37 | 72 | 1.54 |
| 80 Z isomer | — | — | 0.12 |

TOXICOLOGY

The first toxicology studies performed show that the products of the Examples do not induce a deleterious effect in the rat after the oral absorption of doses ranging up to 300 mg/kg.

What is claimed is:

1. A heterocyclic diarylmethylene compound, of general formula (I):

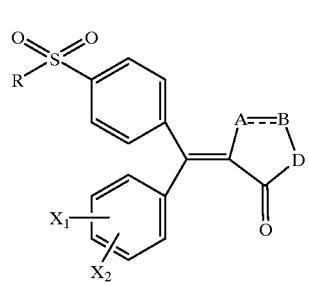

Formula (I)

wherein:
R is:
  a lower alkyl radical having 1 to 6 carbons,
  a lower haloalkyl radical having 1 to 6 carbons,
  an $NH_2$ group,
$X_1$ and $X_2$ independently are:
  a hydrogen atom,
  a halogen atom,
  a lower alkyl radical having 1 to 6 carbons,
  a lower O-alkyl radical having 1 to 6 carbons,
  a trifluoromethyl radical, or two of these together may form a methylenedioxy group,
A is:
  a $CH_2$ group,
  a nitrogen atom
  a sulfur atom,
B is:
  a $CH_2$ group,
  a CH—R' group, wherein R' is a lower alkyl radical having 1 to 6 carbon atoms,
  a C=S group,
  a C-Φ group, Φ being an aromatic ring, wherein A is a nitrogen atom and wherein the bond between A and B is a double bond,
D is:
  an oxygen atom when A is a heteroatom,
  a sulfur atom,
  an N—R" group, in which R" is:
    a hydrogen atom,
    a lower alkyl radical having 1 to 6 carbon atoms,
    an allyl radical,
    a $C_3$-$C_7$ cycloalkyl radical,
    a $(CH_2)_n$—Y radical, wherein n is an integer from 1 to 4, and wherein Y is an OH or COOR'" group, R'" being a hydrogen atom or a lower alkyl radical having 1 to 6 carbon atoms,
    a $(CH_2)_m$—Ar group, wherein m is an integer from 0 to 4, and Ar is an unsubstituted or a substituted phenyl ring having 1 to 3 halogen atoms or 1 to 3 lower alkyl radicals having 1 to 6 carbon atoms,
as well as pharmaceutically acceptable salts thereof.

2. A compound of formula (I) according to claim 1, wherein:
R is:
  a methyl radical, or
  an $NH_2$ group,
$X_1$ and $X_2$ independently are:
  a hydrogen atom,
  a halogen atom,
  a lower alkyl radical having 1 to 6 carbons,
  a lower O-alkyl radical having 1 to 6 carbons, A is:
   a CH₂ group,
   a nitrogen atom
   a sulfur atom, B is:
   a CH₂ group,
   a CH—R' group, wherein R' is a lower alkyl radical having 1 to 6 carbon atoms,
   a C=S group,
   a C-Φ group, Φ being an aromatic ring, wherein A is a nitrogen atom and wherein the bond between A and B is a double bond, D is:
   an oxygen atom when A is a heteroatom,
   a sulfur atom,
   an N—R" group, in which R" is:
      a hydrogen atom,
      a lower alkyl radical having 1 to 6 carbon atoms,
      an allyl radical,
      a $C_3$–$C_7$ cycloalkyl radical,
      a $(CH_2)_n$—Y radical, wherein n is an integer from 1 to 4, and wherein Y is an OH or COOR'" group, R'" being a hydrogen atom or a lower alkyl radical having 1 to 6 carbon atoms,
      a $(CH_2)_m$—Ar group, wherein m is an integer from 0 to 4, and Ar is an unsubstituted or a substituted phenyl ring having 1 to 3 halogen atoms or 1 to 3 lower alkyl radicals having 1 to 6 carbon atoms, as well as pharmaceutically acceptable salts thereof.

3. A compound according to claim 1, wherein R is a methyl radical or an NH₂ group.

4. A compound according to claim 1, wherein $X_1$ is a chlorine atom, and $X_2$ is a hydrogen atom or a chlorine atom.

5. A compound according to claim 1, wherein A and B each represent a CH₂ group.

6. A compound according to claim 1, wherein D is a sulfur atom or an N—CH₃, N—C₂H₅, or N-(3-Cl benzyl) group.

7. A compound according to claim 1, which is selected from the group consisting of:

(Z)-3-[1-(4-chlorophenyl)-1-[4-(methylsulphonyl)phenyl]methylene]dihydro-2(3H)-thiophenone

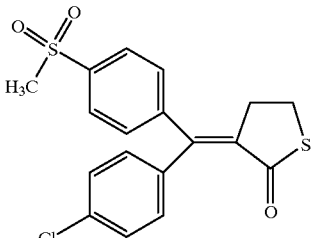

(Z)-3-[1-(4-chlorophenyl)-1-[4-(methylsulphonyl)phenyl]methylene]-1-ethyl-pyrrolidin-2-one

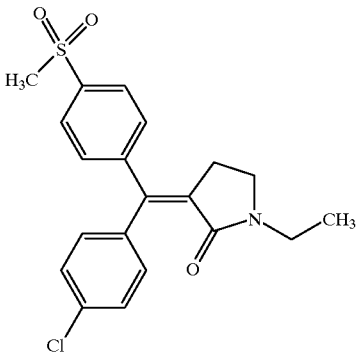

(Z)-3-[1-(3,4-dichlorophenyl)-1-[4-(methylsulphonyl)phenyl]methylene]-1-methyl-pyrrolidin-2-one

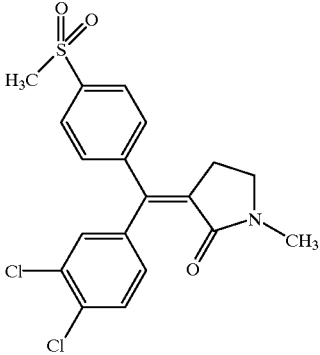

-continued (Z)-4-[(3,4-dichlorophenyl)-(1-methyl-2-oxo-pyrrolidin-3-ylidene)methyl]-benzenesulphonamide

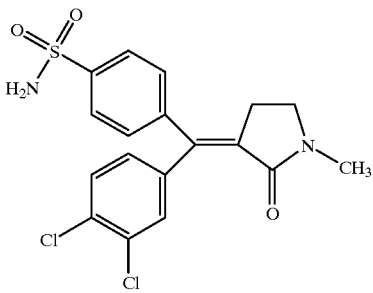

(Z)-3-[1-(4-chlorophenyl)-1-[4-(methylsulphonyl)phenyl]methylene]-1-(3-chlorophenylmethyl)-pyrrolidin-2-one

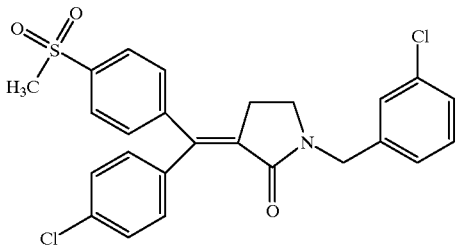

8. A method of preparing compounds of formula (I) according to claim 1, wherein said method comprises the condensation of a ketone of formula:

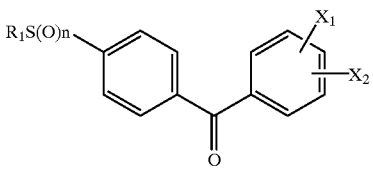

in which $X_1$ and $X_2$ are as defined in claim 1, n is 0 or 2 and $R_1$ is a lower alkyl radical having 1 to 6 carbon atoms, a lower haloalkyl radical having 1 to 6 carbon atoms and can be an NH-tert-butyl radical when n=2, into a compound of formula

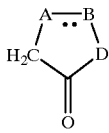

in which A, B, D are as defined in claim 1, in the presence of a base such as potassium tert-butoxide or sodium hydride, or in the presence of titanium tetrachloride and pyridine, in a solvent such as dimethylformamide, tetrahydrofuran or dichloromethane, followed where necessary by a dehydration reaction with sulfuric acid in acetic acid or even trifluoroacetic acid in dichloromethane, it being specified when n equals 0, the compounds obtained are oxidized, for example, with the aid of a peracid, in order to obtain the corresponding compounds of formula (I) in which n equals 2, and when $R_1$ represents an NH-tert-butyl group, the compounds obtained are heated in toluene in the presence of para-toluenesulphonic acid in order to obtain the corresponding compounds of formula (I), in which R represents an $NH_2$ group.

9. A pharmaceutical composition which comprises a pharmaceutically effective amount of at least one compound of formula (I) as defined in claim 1, a pharmaceutically acceptable salt thereof, incorporated in a pharmaceutically acceptable excipient, vehicle or carrier.

10. A pharmaceutical composition with anti-inflammatory and analgesic activity which comprises a pharmaceutically effective amount of at least one compound of formula (I) as defined in claim 1, a pharmaceutically acceptable salt thereof, incorporated in a pharmaceutically acceptable excipient, vehicle or carrier.

11. The pharmaceutical composition according to claim 9, which is presented in the form of gelatin capsules or tablets containing a dose of 1 mg to 1000 mg.

12. The pharmaceutical composition according to claim 9 which is presented in the form of an injectable preparation containing a dose of 0.1 mg to 500 mg.

* * * * *